United States Patent
Shimada

(10) Patent No.: US 6,576,310 B2
(45) Date of Patent: Jun. 10, 2003

(54) NON-STICKY MEDICAL TUBING

(75) Inventor: Mamoru Shimada, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/755,074

(22) Filed: Jan. 8, 2001

(65) Prior Publication Data

US 2001/0021430 A1 Sep. 13, 2001

(30) Foreign Application Priority Data

Jan. 7, 2000 (JP) ........................................ 2000-001407

(51) Int. Cl.$^7$ ............................................... B29D 23/00
(52) U.S. Cl. ..................... 428/36.9; 428/36.92; 525/95; 525/98; 525/240; 525/241
(58) Field of Search ............................ 428/36.9, 36.92; 525/95, 98, 240, 241

(56) References Cited

U.S. PATENT DOCUMENTS

| | | | |
|---|---|---|---|
| 4,327,009 A | 4/1982 | Allen et al. | 524/114 |
| 4,684,576 A | 8/1987 | Tabor et al. | 428/441 |
| 4,948,643 A | 8/1990 | Mueller | 428/36.6 |
| 5,206,301 A | 4/1993 | Hattori et al. | 525/314 |
| 5,272,236 A | 12/1993 | Lai et al. | 526/348.5 |
| 6,162,935 A | 12/2000 | Chen | 556/27 |
| 6,184,291 B1 * | 2/2001 | Ahmed et al. | 525/98 |

FOREIGN PATENT DOCUMENTS

| | | | | |
|---|---|---|---|---|
| JP | 7-241330 | * | 9/1995 | A61J/1/10 |

OTHER PUBLICATIONS

Patent Abstract of Japanese Patent Publication No. 63015957, Publication Date Jan. 23, 1988.

Patent Abstract of Japanese Patent Publication No. 3072512, Publication Date Mar. 27, 1991.

Patent Abstract of Japanese Patent Publication No. 5170844, Publication Date Jul. 9, 1993.

Patent Abstract of Japanese Patent Publication No. 8109288, Publication Date Apr. 30, 1996.

Database JICST–EPLUS 'Online! Shibata Tooru:"Latest technology of synthetic rubber and elastomer. Soft PVC–like olefin material "JSR Dynaron."." retrieved from STN Database accession No. 1000029650 XP002169524 *abstract* & JETI, (1999) vol. 47, No. 12, pp. 143–144. Journal Code: F0013B (Fig. 3, Tbl. 1) ISSN: 0289–4343, Japan.

Database Toxlit 'Online! Takeoka M et al: "Urinary catheters." retrieved from STN Database accession No. 1997:30220 XP002169525 *abstract* & JP 08 299431 A (Terumo Corp.) Nov. 19, 1996.

Database WPI Section Ch, Week 199546 Derwent Publications Ltd., London, GB; AN 1995–354308 XP002169526 & JP 07 241330 A (Terumo Corp), Sep. 19, 1995 *abstract*.

* cited by examiner

Primary Examiner—James J. Seidleck
Assistant Examiner—Melanie Bissett
(74) Attorney, Agent, or Firm—Kubovcik & Kubovcik

(57) ABSTRACT

A medical tubing having rigidity, flexibility, transparency and heat resistance and, additionally, acceptable flexural modulus and tensile strength and further having no stickiness between surfaces of the tubing is provided. The medical tubing is composed of a resin composition containing a low-density ethylene/α-olefin copolymer having a density of 0.860–0.900 g/cm$^3$ polymerized with a metallocene catalyst and a styrene/ethylene-butylene/olefin block copolymer.

5 Claims, No Drawings

NON-STICKY MEDICAL TUBING

FIELD OF THE INVENTION

The present invention relates to a non-sticky tubing that is used as a connecting tube in the medical fields, for instance, infusion solution sets, as extension tubing, tubing for blood circuits, tubing for blood transfusion, joint tubing, tubing for winged needles, and the like.

BACKGROUND OF THE INVENTION

Medical tubing used as connecting tubing for infusion solution sets, blood circuits and the like must be excellent in flexibility, rigidity, transparency and heat resistance. Therefore, soft vinyl chloride resins have heretofore been used as a base material. However, the soft vinyl chloride resins contain a large amount of dioctyl phthalate or 2-ethylhexyl phthalate as a plasticizer and the elution of such a plasticizer into the infusion solution, blood, etc. causes safety problems. In addition, the soft vinyl chloride resins adsorb lipid soluble drug components such as nitroglycerine, isosorbide nitrate and diazepam so that when drugs containing such components are administered to patients, it is very difficult to administer exactly the necessary amounts of the drugs.

As a medical base material developed in consideration of the above problems, attention has been paid to polyethylene type resins. For example, tubing formed of ultra-low density polyethylene having a specific gravity of 0.89 or less (JP-B-Hei 1-48775) has been known. This resin is excellent in transparency but has a broad molecular weight distribution and includes low molecular weight components. As a result, tubing molded from this resin tends to be sticky and the inner surfaces of the tubing tend to stick to each other. Furthermore, once the tubes are folded, it takes a long time for the original configuration to be recovered and medical care may sometimes be interrupted.

To improve this problem, use of low-density polyethylenes and thermoplastic α-olefin resins prepared with metallocene catalysts has been proposed. However, although tubing molded from these resins is slightly less sticky than tubing molded from resins prepared without the use of metallocene catalysts, the resins have low tensile strengths and tubing molded therefrom has a defect that it tends to be cut.

Furthermore, a blended resin composed of a linear low-density polyethylene having a density of 0.92–0.94 g/cm$^3$ and a thermoplastic polystyrene elastomer and a blended resin obtained by blending a thermoplastic polyolefin elastomer with these resins (JP-B-Hei 2-31989) have also been known. As the thermoplastic polystyrene elastomer, there are disclosed styrene/butadiene/styrene elastomer, styrene/ethylene-butylene/styrene elastomer, styrene/ethylene/butadiene/styrene elastomer and styrene/isoprene/styrene elastomer. However, tubing made of these blended resins have smaller flexural moduli than tubing formed of an ethylene type resin alone. Although stickiness of the tubing may be decreased depending on the ratio of the blended resins, the tubing tends to be broken since it also has low tensile strength.

Under the above-described circumstances, an object of the present invention is to provide a medical tubing which has not only rigidity, flexibility, transparency and heat resistance but also acceptable flexural modulus and tensile strength, and further, shows no stickiness between surfaces of the tubing.

SUMMARY OF THE INVENTION

The present inventors have carried out extensive research and as a result have found that a blend of an ethylene copolymer prepared with a metallocene catalyst and a specified thermoplastic polystyrene elastomer can avoid the above problems, thereby achieving the present invention.

The present invention relates to a medical tubing comprising a resin composition containing a low-density ethylene/α-olefin copolymer having a density of 0.860–0.900 g/cm$^3$ polymerized with a metallocene catalyst and a styrene/ethylene-butylene/olefin block copolymer.

In the present invention, the low-density ethylene/α-olefin copolymer is a copolymer prepared by polymerizing ethylene and α-olefin with a metallocene catalyst. The lower density ethylene/α-olefin copolymer having a density of 0.860–0.900 g/cm$^3$ polymerized with a metallocene catalyst is commercially available and can be prepared by a method as described in U.S. Pat. Nos. 4,327,009, 4,684,576, 5,272,236, and 6,162,935,the disclosures of which are incorporated herein by reference The low-denisty ethylene/α-olefin copolymer prepared with a metallocene catalyst has a density of 0.860–0.900 g/cm$^3$, and preferably 0.870–0.900 g/cm$^3$. If the density is lower than 0.860 g/cm$^3$, medical tubing prepared using the copolymer has low tensile strength. If the density is higher than 0.900 g/cm$^3$, medical tubing prepared using the copolymer has too small flexural modulus so that it tends to be folded.

The molecular weight distribution, (Mw (weight average molecular weight)/Mn (number average molecular weight)) of the low-density ethylene/α-olefin copolymer prepared with a metallocene catalyst is 1.8–2.5, which is narrower than the molecular weight distribution of 3.0–4.5 of the ethylene copolymer prepared without a metallocene catalyst. This results in low stickiness of the medical tubing made from the copolymer, so that there is no fear that the inner surfaces of the tubing will stick to each other.

The molecular weight (number average molecular weight) of the low-density ethylene/α-olefin copolymer is 20,000–250,000, and preferably 30,000–150,000. If the molecular weight is less than 20,000, tubing made from the copolymer has poor heat resistance while, if it is more than 250,000, tubing made from the copolymer has low transparency. Neither case is desirable.

The α-olefin contained in the above low density ethylene/α-olefin copolymer is preferably one having 4–8 carbon atoms and specific examples thereof include butene-1, pentene-1, 4-methyl-1-pentene, hexene-1, and octene-1. Specific examples of the copolymer include ethylene/butene-1 copolymer, ethylene/pentene-1 copolymer, ethylene/4-methyl-1-pentene copolymer, ethylene/hexene-1 copolymer and ethylene/octene-1 copolymer. More preferably, ethylene/octene-1 copolymer is used.

The α-olefin content in the low density ethylene/α-olefin copolymer is 10–50% by weight, and preferably 15–45% by weight. If the content is less than 10% by weight, medical tubing made from the copolymer has too large a flexural modulus and if it is more than 50% by weight, medical tubing made from the copolymer has high stickiness.

In the present invention, the styrene/ethylene-butylene/ olefin block copolymer is a copolymer composed of a polystyrene block, an ethylene-butylene copolymer block, and a polyolefin block The copolymer is commercially available and is described, for example in U.S. Pat. No. 5,206,301 and Japanese Patent Application Laid Open Nos. Hei 3-72512, Hei 5-170844 and Hei 8-109288, the disclosures of which are incorporated herein by reference.

The monomer that constitutes the polystyrene block includes styrene and its derivatives, for example, p-methylstyrene, t-butylstyrene, vinylpyridine, and α-methylstyrene.

The ethylene-butylene copolymer block is one obtained by hydrogenation of 80% or more, and preferably 90% of a polybutadiene block. If the ratio of hydrogenation is less than 80%, the copolymer is cross-linked by γ rays, light, or heat when it is sterilized, causing a fear that medical tubing made from the copolymer will have too high a hardness.

The polyolefin block is such that the polyolefin is preferably crystallized since this makes it possible to form tubing having flexibility of the same level as that of tubing made of conventional thermoplastic polystyrene elastomers but which is rich in strength. The olefin is preferably one having 2–8 carbon atoms, specific examples of which include ethylene, propylene, and butene-1. Ethylene is preferred in view of affinity for low-density ethylene/α-olefin.

The styrene content of the styrene/ethylene-butylene/ olefin block copolymer is preferably 5–50% by weight. A block copolymer having a styrene content of 10–40% by weight is preferred for obtaining medical tubing that has small flexural modulus and is excellent in flexibility.

The hardness of the above copolymer is 35–85 (Shore A, ASTM D2240), and preferably 60–80. If the hardness is less than 35, medical tubing using the copolymer has too small a flexural modulus so that once it is folded, recovery to the original configuration takes a long time. If the hardness is larger than 85, conversely, the flexural modulus is too large so that the flexibility of the tubing is insufficient.

The low-density ethylene/α-olefin copolymer content in the resin composition of the present invention is 10–90% by weight, preferably 20–80% by weight, and more preferably 30–70% by weight. If the content is less than 10% by weight, medical tubing made from the resin composition tends to adhere on the inner surfaces thereof. If it is more than 90% by weight, the stickiness of the tubing increases again and further the tensile strength is too low so that the tubing tends to be cut.

The resin composition in the present invention may contain styrene elastomers other than the above styrene/ ethylene-butylene/olefin block copolymer in an amount such that the flexural modulus and tensile strength of medical tubing composed of the resin composition will not be deteriorated. The other styrene elastomers include, for example, styrene/ethylene-butylene/styrene block copolymers, styrene/ethylene/propylene/styrene block copolymers, styrene/butylene/styrene block copolymers, and styrene/isoprene/styrene block copolymers.

The resin composition in the present invention may further contain a lubricant in order to prevent adhesion between the inner surfaces of the medical tubing or to decrease frictional resistance on the outer surface of the tubing. Suitable lubricants include silicone, triglycerides, stearic acid metal salts, fatty acid amides, higher fatty acid waxes, fatty acid waxes and the like.

Furthermore, the resin composition in the present invention may contain additives such as anti-blocking agents and antioxidants in an amount such that the properties of the resin composition are not deteriorated.

Medical tubing composed of the resin composition of the present invention can be obtained by melt-kneading pellets of respective polymers of the resin composition with a twin-screw extruder or the like and extrusion-molding the product in a single-screw extrusion molding machine or the like in a tubular form. Alternatively, pellets of respective polymers each dry-blended directly with a single-screw extrusion-molding machine may be extrusion molded into a tubular form.

The medical tubing of the present invention is preferably one that has a flexural modulus of 100 $kgf/cm^2$ or less and a tensile strength of 100 $kgf/cm^2$ or more. If the flexural modulus is greater than 100 $kgf/cm^2$, the tubing is too hard and tends to kink. If the tensile strength is lower than 100 $kgf/cm^2$, the tubing tends to be cut.

In the present invention, the term "tubing" means a pipe or conduit whose cross section is circular and, in order to be useful as a medical tubing, preferably has an inner diameter of 1 mm or more and an outer diameter of 1.5 mm or more. The length of the tubing is not particularly limited but is preferably 30 mm or more in order to be used as a medical tubing.

The medical tubing of the present invention may be either a single layer tubing made of the resin composition of the present invention or a multi-layer tubing made of a laminate of the resin composition and other resin(s). As the other resin, ethylene/vinyl acetate copolymer, styrene/ethylene-butylene/styrene copolymer and the like may be used.

The medical tubing thus obtained may be used as a medical tubing for infusion solution sets, extension tubing, tubing for blood circuits, for blood transfusion, joint tubing, tubing for wing-like needles, etc. The medical tubing of the present invention is excellent not only in flexural modulus and tensile strength but also in transparency and has no stickiness between the tubing and therefore it is more preferred that it be used as a tubing for an infusion solution.

DESCRIPTION OF PREFERRED EMBODIMENTS

Hereinafter, the present invention will be described in more detail in conjunction with specific embodiments.

However, the present invention is not limited thereto. In the examples, each measurement and observation was made as follows.

Measurements of Flexural Modulus and Tensile Strength and Observation of Transparency and Stickiness The flexural modulus was obtained by using the tubing as it is as a sample, measuring its flexural stress in accordance with JIS K7171 and calculating a modulus according to the calculation formula for the flexural modulus of a cylinder. In this case, measurement of flexural stress was performed by 3 point bending at a cross-head speed of 1 mm/minute and at a distance of 8 mm between the supporting points.

The tensile strength was measured by using the tubing as it is as a sample and measuring strength at break in accordance with JIS K7113, "Tensile Test Method for Plastics". In this case, the cross-head speed was 200 mm/minute and the distance between the nippers was 20 mm.

The transparency of the tubing was visually observed and when bubbles in physiological saline that had flowed into the tubing were observed, the sample was judged to have transparency.

The stickiness of the tubing was judged based on the stickiness of the outer surface and of the inner surface of the tubing. The stickiness of the outer surface of the tubing was judged to be non-sticky when two pieces of tubing in close contact that had been inserted into a stainless steel pipe having an inner diameter of 6 mm and taken out therefrom after 30 minutes can be separated, or sticky when the tubing is separated but gave a gummy feel or remained in close contact. The stickiness of the inner surface in the above tubing was judged to be non-sticky when the tubing that had been left to stand for 1 minute in a folded state and the folding force had been thereafter removed showed a recovery from the yield of the folded portion of the tubing within 5 seconds, or sticky when it did not show such a recovery.

EXAMPLES 1–12

COMPARATIVE EXAMPLES 1–3

Metallocene catalyst-prepared ethylene/octene copolymers (A) of different densities and a styrene/ethylene-butylene/ethylene block copolymer (B) (DYNARON$^R$ 4600P manufactured by JSR Corporation, styrene content 20%, gravity 0.91, MFR 10 g/10 cm and Shore A 78) shown in Table 1 were mixed in various mixing ratios. The resulting pellets of the resin compositions were melt kneaded by a twin-screw extruding machine (PCM30, manufactured by Ikegai Tekko Co., Ltd.) and molded with a single-screw extrusion molding machine (UT-25-1, manufactured by Plastics Engineering Research Institute Co., Ltd.) into a tubing of 3.6 mm in outer diameter and 2.3 mm in inner diameter. All of the tubing in Examples 1–12 passed the self-regulated standard "Medical Polyethylene" by the Medical Material Association. The results of measurements or observations on the flexural modulus, tensile strength, transparency and stickiness of the tubing are shown in Table 1.

TABLE 1

|  | Density of copolymer (A) (g/cm$^3$) | Mixing ratio (A)/(B) | Flexural modulus (kgf/cm$^2$) | Tensile strength (kfg/cm$^2$) | Transparency ○: Yes X: No | Stickiness ○: Non-sticky X: Sticky | |
|---|---|---|---|---|---|---|---|
|  |  |  |  |  |  | Outer Surface | Inner Surface |
| Example 1 | 0.870*1 | 70/30 | 41 | 117 | ○ | ○ | ○ |
| Example 2 | 0.880*2 | 70/30 | 53 | 124 | ○ | ○ | ○ |
| Example 3 | 0.885*3 | 70/30 | 76 | 130 | ○ | ○ | ○ |
| Example 4 | 0.895*4 | 70/30 | 92 | 142 | ○ | ○ | ○ |
| Example 5 | 0.900*5 | 70/30 | 97 | 153 | ○ | ○ | ○ |
| Example 6 | 0.870*1 | 20/80 | 34 | 154 | ○ | ○ | ○ |
| Example 7 | 0.870*1 | 40/60 | 37 | 138 | ○ | ○ | ○ |
| Example 8 | 0.870*1 | 60/40 | 40 | 122 | ○ | ○ | ○ |
| Example 9 | 0.870*1 | 80/20 | 42 | 108 | ○ | ○ | ○ |
| Example 10 | 0.900*5 | 40/60 | 59 | 158 | ○ | ○ | ○ |
| Example 11 | 0.900*5 | 60/40 | 77 | 161 | ○ | ○ | ○ |
| Example 12 | 0.900*5 | 80/20 | 89 | 160 | ○ | ○ | ○ |
| Comparative Example 1 | 0.870*1 | 0/100 | 32 | 173 | ○ | ○ | X |
| Comparative Example 2 | 0.870*1 | 100/0 | 44 | 85 | ○ | ○ | X |
| Comparative Example 3 | 0.905*6 | 70/30 | 105 | 169 | ○ | ○ | ○ |

*1:ENGAGE 8200,
*2:ENGAGE 8411,
*3:ENGAGE 8585,
*4:AFFINITY PF1140,
*5:Niporon-Z 7P04A,
*6:Carnel 55FI,

*1, *2, *3 and *4 are manufactured by The Dow Chemical Company. *5 is manufactured by Toso Corporation. *6 is manufactured by Mitsubishi Chemicals.

As is apparent from Table 1, the medical tubing of the present invention is excellent in each of flexural modulus, tensile strength, transparency and stickiness. On the other hand, as shown in the Comparative Examples, tubing made from one of copolymer (A) and copolymer (B)

(Comparative Examples 1 and 2) show stickiness. Additionally, when the density of the copolymer (A) exceeds the range of the present invention (Comparative Example 3), the flexural modulus of the tubing increases and the tubing becomes harder so that there is a fear that it cannot be used as a medical tubing.

COMPARATIVE EXAMPLES 4 AND 5

Metallocene catalyst-prepared ethylene/octene copolymer (A) having a density of 0.880 g/cm³ (ENGAGE 8411 manufactured by The Dow Chemical Company) and a styrene/ethylene-butylene/styrene block copolymer (B') (CRATON G-1657 manufactured by Shell Corporation, block ratio of styrene/ethylene-butylene 13/87 (wt. %), gravity 0.92, melt index 8 g/10 min and Shore A 65) were mixed in various mixing ratios shown in Table 2, and tubing was prepared using the resulting pellets of the resin compositions in the same manner as in Example 1. The tubing was measured or observed for flexural modulus, tensile strength, transparency and stickiness. The results are shown in Table 2.

TABLE 2

| | Mixing ratio (A)/(B') | Flexural modulus (kgf/cm²) | Tensile strength (kfg/cm²) | Transparency ○: Yes X: No | Stickiness ○: Non-sticky X: Sticky | |
|---|---|---|---|---|---|---|
| | | | | | Outer Surface | Inner Surface |
| Comparative Example 4 | 20/80 | 16 | 93 | ○ | ○ | X |
| Comparative Example 5 | 40/60 | 28 | 97 | ○ | ○ | X |

As is apparent from Table 2, the tubing made from styrene/ethylene-butylene/styrene block copolymer (B') in place of styrene/ethylene-butylene/ethylene block copolymer (B) has stickiness. The tensile strength thereof is smaller than the tubing made from the copolymer (B).

COMPARATIVE EXAMPLE 6, 7 AND 8

Ziegler-Natta catalyst-prepared low-density polyethylene (A') (Polyethylene ZN; EUL 130 manufactured by Sumitomo Chemicals) and styrene/ethylene-butylene/ethylene block copolymer (B) (DYNARON$^R$ 4600P manufactured by JSR Corporation) were mixed in various mixing ratios shown in Table 3, and tubing was prepared using the resulting pellets of resin compositions in the same manner as in Example 1. The tubing was measured or observed for flexural modulus, tensile strength, transparency and stickiness. The results are shown in Table 3.

TABLE 3

| | Mixing ratio (A')/(B) | Transparency ○: Yes X: No | Stickiness ○: Non-sticky X: Sticky | |
|---|---|---|---|---|
| | | | Outer Surface | Inner Surface |
| Comparative Example 6 | 40/60 | ○ | X | X |
| Comparative Example 7 | 60/40 | ○ | X | X |
| Comparative Example 8 | 90/10 | ○ | X | X |

As is apparent from Table 3, the tubing made from Ziegler-Natta catalyst-prepared low-density polyethylene (A') in place of metallocene catalyst-prepared ethylene/octene copolymer (A) has stickiness. As for the flexural modulus and tensile strength of the tubing, it already had stickiness and was judged to be unfit as a medical tubing, so that no further measurement was performed.

Since the medical tubing of the present invention uses styrene/ethylene-butylene/olefin block copolymer, it has excellent flexural modulus and tensile strength so that the tubing hardly kinks. Furthermore, since it uses an ethylene/α-olefin copolymer that has a narrow molecular weight distribution and a small amount of low molecular weight components, sticking between the tubes will not occur and the tubing shows a quick recovery in shape when it is held by roller clamps or when it is folded and it does not disturb in medical care activities.

Furthermore, when the medical tubing of the present invention is stored in an outer wrapper, the tubing will not stick to the outer wrapper so that the tubing can be inserted and extracted without difficulty. After the tubing is stored in the outer wrapper and then taken out therefrom, there is no fear that the outer surfaces of the tubing will stick to each other.

What is claimed is:

1. A medical tubing comprising a resin composition containing 10–90% by weight of a low-density ethylene/α-olefin copolymer having a density of 0.860–0.900 g/cm³ and which is polymerized with a metallocene catalyst, and a styrene/ethylene-butylene/olef in block copolymer, said composition being in the form of tubing that has a flexural modulus of 100 kgf/cm² or less and a tensile strength of 100 kgf/cm² or more.

2. The medical tubing as claimed in claim 1, wherein the ethylene/α-olefin copolymer is an ethylene/octene-1 copolymer having a density of 0.870–0.900 g/cm$^3$.

3. The medical tubing as claimed in claim 1, wherein the styrene/ethylene-butylene/olefin block copolymer is a block copolymer having a styrene content of 5–50% by weight and a hardness of 35–85 (Shore A, ASTM D2240).

4. The medical tubing as claimed in claim 1, wherein the styrene/ethylene-butylene/olefin block copolymer is a styrene/ethylene-butylene/ethylene block copolymer.

5. An infusion solution set comprising the medical tubing as claimed in claim 1 as a connector.

* * * * *

UNITED STATES PATENT AND TRADEMARK OFFICE
CERTIFICATE OF CORRECTION

PATENT NO.    : 6,576,310 B2
DATED         : June 10, 2003
INVENTOR(S)   : Mamoru Shimada It is certified that error appears in the above-identified patent and that said Letters Patent is hereby corrected as shown below:

Column 8,
Line 63, "styrene/ethylene-butylene/olef in block copolymer, said" should be
-- styrene/ethylene-butylene/olefin block copolymer, said --.

Signed and Sealed this

Twelfth Day of August, 2003

JAMES E. ROGAN
*Director of the United States Patent and Trademark Office*